United States Patent

Kardum et al.

[11] Patent Number: 5,775,579
[45] Date of Patent: Jul. 7, 1998

[54] REFUSE AIRLOCK

[75] Inventors: Iwe Kardum, Neuotting; Rudolf Ebner, Rattenkirchen, both of Germany

[73] Assignee: InnoRatio Aktiengesellschaft fur innovative umwelttechnische System i.Gr., Germany

[21] Appl. No.: 593,876

[22] Filed: Jan. 30, 1996

[51] Int. Cl.$^6$ .................................................. B65D 91/00
[52] U.S. Cl. ................................................ 232/43.1; 49/35
[58] Field of Search ........................... 232/43.1, 43.4, 232/44, 41 A, 41 B, 41 C, 41 D

[56] References Cited

U.S. PATENT DOCUMENTS

| | | | |
|---|---|---|---|
| 1,038,583 | 9/1912 | Hodgkinson | 232/41 D |
| 1,046,784 | 12/1912 | Hartman | 232/41 D |
| 1,979,405 | 11/1934 | Payne | 232/41 B |
| 3,742,647 | 7/1973 | Tomita | 49/35 |
| 4,525,951 | 7/1985 | Williams | 49/35 X |
| 5,333,410 | 8/1994 | Tetherton | 49/35 |

Primary Examiner—Jerry Redman
Attorney, Agent, or Firm—Anthony J. Casella; Gerald E. Hespos; Ludomir A. Budzyn

[57] ABSTRACT

The present invention relates to a refuse airlock (10) for refuse bins or refuse containers, having a closable inlet (20) for introducing waste material and a closable outlet (30) for discharging the waste material, wherein the inlet (20) and the outlet (30) are not open at the same time, at least one controllable interlock is provided for the inlet (20) and/or outlet (30), a payment device is provided, which controls the interlock in dependence on a payment or cost calculation operation, the inlet (20) comprises a first closure device (22) which is (mechanically) connected to the outlet (30) and has a pivoting and/or sliding or slide closure, and the outlet (30) has a pivoting and/or sliding or slide closure (32).

18 Claims, 3 Drawing Sheets

REFUSE AIRLOCK

BACKGROUND OF THE INVENTION

1. Field of the Invention

The present invention relates to a refuse airlock for refuse bins or refuse containers.

2. Description of the Prior Art

Refuse flaps for throwing in refuse are already known, which flaps have an opening through which the refuse is thrown in. In the known refuse flaps, however, the waste material can be thrown in through the opening by anyone, and it is thus impossible to allocate the refuse to individuals or several persons within a group, e.g. to different tenants of an apartment building. Furthermore, in apartment buildings, the refuse costs are divided up proportionately according to living area, as a result of which an individual tenant, for example, in a large apartment pays more than two tenants in a smaller apartment although it can be proved that two tenants generate and dispose of more waste material than a single one. The division of the refuse costs is thus unfair and the proportions to be paid by the individual parties do not correspond to the volume of refuse actually generated by them. There is thus no incentive to avoid generating refuse.

DE-A-41 42 206 discloses an input control device for refuse containers in which a housing is supported on a stand in which a refuse container which is open at the top is positioned. The housing has a door at the front which can be opened after the insertion of a token so that a bag can be placed on the floor of the housing. After the door is closed, the floor is drawn away manually or by motor so that the refuse bag drops into the refuse container. This known input control device has, however, the disadvantage that if the user who has put a refuse bag into the input control device omits to activate the floor manually or by motor, a subsequent user who inserts a token and opens the front door finds the input control device already filled with refuse and cannot dispose of his own refuse. Furthermore, the motor for driving the floor may fail. Advantageously reliable and practical disposal of refuse is therefore not possible.

DE-A-39 11 971 discloses a collection device for special refuse, which device has closed boxes into which special waste can be introduced through flaps. The closed, full boxes are then transported away by means of pallets for weighing and emptying while further, empty boxes are arranged in their place. However, this known collection device is complicated in construction and is therefore, in particular, not suitable for the disposable of ordinary domestic refuse.

SUMMARY OF THE INVENTION

According to the invention, this object is achieved by a refuse airlock in accordance with claim 1. Preferred embodiments of the invention are the subject-matter of the subclaims.

According to the invention, a refuse airlock is provided for refuse bins or refuse containers, having a closable inlet for introducing waste material and a closable outlet for discharging the waste material, the inlet and the outlet not being open at the same time, at least one controllable interlock being provided for the inlet and/or outlet, a payment device being provided, which controls the interlock in dependence on a payment or cost calculation operation, the inlet comprising a first closure device which is connected, in particular mechanically, to the outlet and has a pivoting and/or sliding or slide closure, and the outlet having a pivoting and/or sliding or slide closure.

The refuse airlock according to the invention has two pivoting and/or sliding or slide closure devices which are mechanically connected. After a user has unlocked the interlock, for example by means of a payment operation, he can insert refuse into the refuse airlock through the front sliding closure device. Owing to the mechanical coupling of the two sliding closure devices, when actuating the front sliding closure device, he simultaneously also actuates the sliding closure device of the outlet, as a result of which any refuse having been introduced previously is let out of the refuse airlock. The refuse airlock according to the invention thus guarantees reliable refuse disposal.

Furthermore, the refuse airlock according to the invention is very simple in construction and can thus be designed to be sturdy and fail-safe for a long period.

By means of the refuse airlock according to the invention, protection against fraudulent use by refuse being thrown into the refuse bin or the refuse container by others is guaranteed.

Furthermore, with the refuse airlock according to the invention, it is advantageously possible for refuse costs to be divided up among a group of persons in such a way that this division takes place proportionately in dependence on the quantity of refuse actually introduced into the refuse airlock. A fair division of the refuse costs is thus advantageously guaranteed.

Furthermore, the refuse airlock according to the present invention advantageously offers an incentive to avoid generating refuse or to separate refuse since, owing to the payment or cost calculation operation, every individual has to pay for the refuse introduced by him, thus promoting an awareness of waste material. The refuse airlock according to the invention therefore surprisingly becomes ecologically very important.

In an advantageous development of the present invention, the inlet is connected to the outlet via a chamber which has a predetermined volume, in particular about 20 liters.

It is thus advantageously guaranteed that a specific maximum quantity of waste material or refuse can be introduced or inserted into the refuse airlock in one refuse discharge operation, and the cost calculation or the division of the refuse costs to individual persons or parties is not subject to an uncertainty factor with regard to the quantity of waste material introduced and is thus fairer.

The predetermined volume of the chamber, in particular the 20 liter volume which is advantageous per se, allows the chamber to be adapted to the standard sizes of refuse bins for houses or apartments, thus guaranteeing an advantageous, optimum utilization of the chamber available in a single refuse-discharge operation.

In an advantageous embodiment of the present invention, the outlet is connected to the inlet in such a way that the outlet is closed when the inlet is open.

In an advantageous manner, this thus avoids waste material being discharged without a charging or cost calculation or payment operation, thus making a reliable cost calculation possible and guaranteeing a fairer division of the refuse costs.

In a further preferred embodiment of the present invention, the inlet comprises a first, in particular front, and a second, in particular rear, closure device, the front closure device being connected to the outlet, and the interlock acting on the rear closure device.

In this advantageous embodiment, the inlet is secured by two closures, which advantageously substantially improves the security against fraudulent use. Additionally, the connection or coupling between the inlet and/or outlet and the interlock, i.e. the locking operation, is interrupted or discontinuous, as a result of which a further advantageous increase in the operating reliability or security against fraudulent use is achieved.

The rear closure device of the inlet of the refuse airlock is preferably only accessible when the front closure device is open. The front closure device is furthermore preferably not closable when the rear closure device is open. With greatest preference, the front closure device has a pivoting or sliding or slide closure.

It is thus advantageously guaranteed that the refuse airlock does not permit simultaneous opening of the inlet and of the outlet in any circumstances, thus preventing any avoidance of the payment operation.

In a further embodiment of the present invention, the first, in particular front, closure device is connected to the outlet via at least one wire cable guided around deflection rollers.

This connection or coupling between the inlet and the outlet is particularly sturdy and thus advantageously increases the operational reliability and service life of the refuse airlock.

According to a preferred embodiment, the first closure device and the outlet comprise closure elements connected to one another in an articulated manner, the closure elements being of elongate design and being guided in rails at their end faces. In particular, the first closure device and the outlet can be designed as a single link chain formed from closure elements connected in an articulated manner.

In this preferred embodiment, the inlet and the outlet are advantageously of simple and sturdy design and allow simple opening and closure of the inlet or outlet tube.

In a further preferred embodiment, a restoring mechanism is provided, which prestresses the inlet and/or the outlet into an original position.

It is thus advantageously guaranteed that the refuse airlock is normally, i.e. in an unactuated state, in a closed position, thus preventing the insertion of refuse, for example, by unauthorized persons, that is to say insertion of refuse by others. The security against fraudulent use is thus advantageously increased.

In a further preferred development of the invention, a weighing device is provided for weighing the waste material introduced into the refuse airlock.

This measure allows a weight-related cost calculation or payment for the waste material introduced or discharged into the refuse airlock. The refuse costs of individual households or apartment buildings are calculated by the local councils or parishes in volumes or units of volume whereas, with the waste disposal companies, the local councils calculate costs according to weight. Efforts are therefore being made advantageously already to calculate costs according to weight, for the waste material occurring, at the source, i.e. in the households in order to guarantee a fairer cost calculation which gives the people an incentive to avoid generating refuse and/or to separate refuse. Such a weight dependent cost calculation for refuse is advantageously made possible in this embodiment of the refuse airlock according to the invention.

In a furthermore preferred embodiment of the present invention, an identification device is provided, which provides the waste material introduced into the refuse airlock, in particular in the form of bags, with an identification.

The identification device, preferably in conjunction with the payment device, advantageously allows the person or party who has introduced the waste material into the refuse airlock to be identified. If, for example, a person introduces impermissible waste material into the airlock, the possibility is thus advantageously provided to impose sanctions for this action. Individual persons are thus advantageously made to behave in an ecologically responsible way.

In a further preferred embodiment of the present invention, the payment device has a charging memory for storing cost calculation operations. The payment device furthermore preferably has a magnetic card recording device which most preferably comprises a scanning device for scanning data of a magnetic card, a memory and a comparison device, the comparison device comparing the data from the scanning device with that from the memory.

In these preferred embodiments, each individual use of the refuse airlock by persons in possession of a magnetic card can advantageously be stored, an authorization check, in particular, being carried out, specifically preferably based on data which are stored internally in a memory.

In a further development of the present invention, the payment device has a code recording device for recording a code which preferably comprises an input unit for the input of a code, a memory and a comparison device, the comparison device comparing the code of the input unit with data stored in the memory.

In these advantageous developments, the use of the refuse airlock is only permitted for those who have or know an appropriate code, thus causing or triggering a payment or charging operation. This thus effectively prevents refuse being thrown into the refuse airlock by others, thus improving the security against fraudulent use.

In a further preferred embodiment of the present invention, the payment device comprises a coin insertion device. The payment device furthermore preferably has a subtraction device and a reading/writing device for reading in or entering a credit, the subtraction device subtracting a unit from the credit and entering the new amount.

These provisions for payment allow advantageous, simple and reliable payment for the refuse introduced into the refuse airlock. A particular advantage can be seen in the fact that various payment systems are used in many machines which are accessible to the public, as a result of which the individual parts or components which are used in the refuse airlock according to the invention are produced in large quantities and are thus advantageously cost-effective and are distinguished by a high degree of operational reliability and security against fraudulent use.

According to a further preferred embodiment, the payment device comprises a data transmission device for transmitting data to a data recording device, the data transmission device in particular transmitting the data by radio and/or via a data transmission network and/or via the telephone network and/or via data memories, the data transmitted particularly preferably comprising individual data or a plurality of sequential data: a date, a time, a code identifying the individual payment device, a code identifying the individual refuse airlock, a filling level of the refuse bin or the refuse container, a number of payment or cost calculation operations carried out in total, a user code, a number of payment or cost calculation operations for a predetermined or predeterminable user code and/or a weight of the waste material inserted.

BRIEF DESCRIPTION OF THE DRAWINGS

Further features, objects and advantages of the present invention will emerge from the following description of examples of preferred embodiments with reference to the drawing, in which.

DETAILED DESCRIPTION OF THE PREFERRED EMBODIMENT

Figure 1:
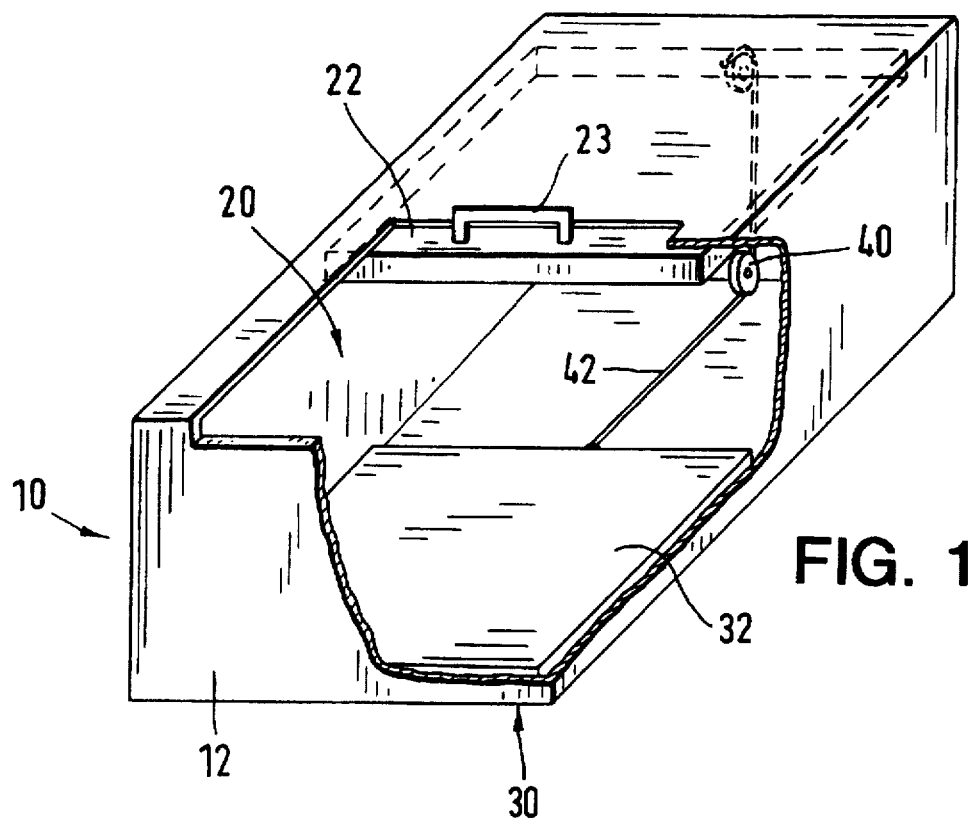
FIG. 1 is a perspective view of an embodiment of the refuse airlock according to the invention.

The refuse airlock 10 illustrated in FIG. 1 comprises a housing 12, a closable inlet 20, through which refuse or waste material can be introduced into a chamber of the refuse airlock 10, and furthermore an outlet 30 through which the waste material drops or is conducted away or discharged from the refuse airlock into a refuse bin or refuse container arranged below the airlock.

The inlet 20 has a slide closure or a sliding lock or sliding door 22 which can close the inlet 20. The slide closure 22 preferably slides on rails or bearings (not illustrated) and is moved or operated manually by means of a handle 23.

The outlet 30 of the refuse airlock 10 is arranged, in particular, on the bottom of the airlock 10 and is in alignment, in particular in vertical alignment, with the inlet 20. The outlet 30 comprises a slide closure 32 which can completely close the opening of the outlet 30 and, in particular, has a similar shape to the slide closure 22 of the inlet.

The slide closures 22 and 32 are connected or coupled to one another, specifically by means of a wire cable 42 which is guided over deflection rollers 40 and consists, in particular, of steel, said deflection rollers having, in particular, guide grooves for the wire cable in circumferential direction. In particular, further wire cables (not illustrated) guided around deflection rollers are provided in order constantly to transmit a tensile force between the interconnected inlet 20 and outlet 30. These wire cables (not illustrated) are guided, in particular, along the side faces of the refuse airlock 10 in order not to obstruct or at least partially close the inlet 20 and/or the outlet 30.

When, in particular, the inlet 20 is actuated or moved, this connection or coupling causes the outlet 30 to move in the opposite direction, thus guaranteeing that, when the inlet 20 is opened or open, the outlet 30 is closed or impassable and, when the inlet 20 is closed, the outlet 30 is open or passable.

The refuse airlock 10 furthermore has a payment device (not illustrated) which controls or regulates or inhibits an interlock (not illustrated). In particular, this interlock locks the inlet 20 and prevents it being actuated or opened. After a cost calculation or charging or payment operation has been carried out, the payment device gives off a signal which inhibits the interlock and thus releases the inlet 20 for opening or actuation.

The payment device comprises a charging memory in which the charges, in particular for different users, are stored. In particular, the payment device comprises a code recording device (not illustrated), by means of which a user of the refuse airlock 10 enters a recognition code to identify himself. After the user has entered the recognition code, the payment device transmits a signal to the interlock, as a result of which the latter is inhibited, and transmits a further signal to the charging memory, as a result of which a charge charged to the user identified takes place.

Figure 2:
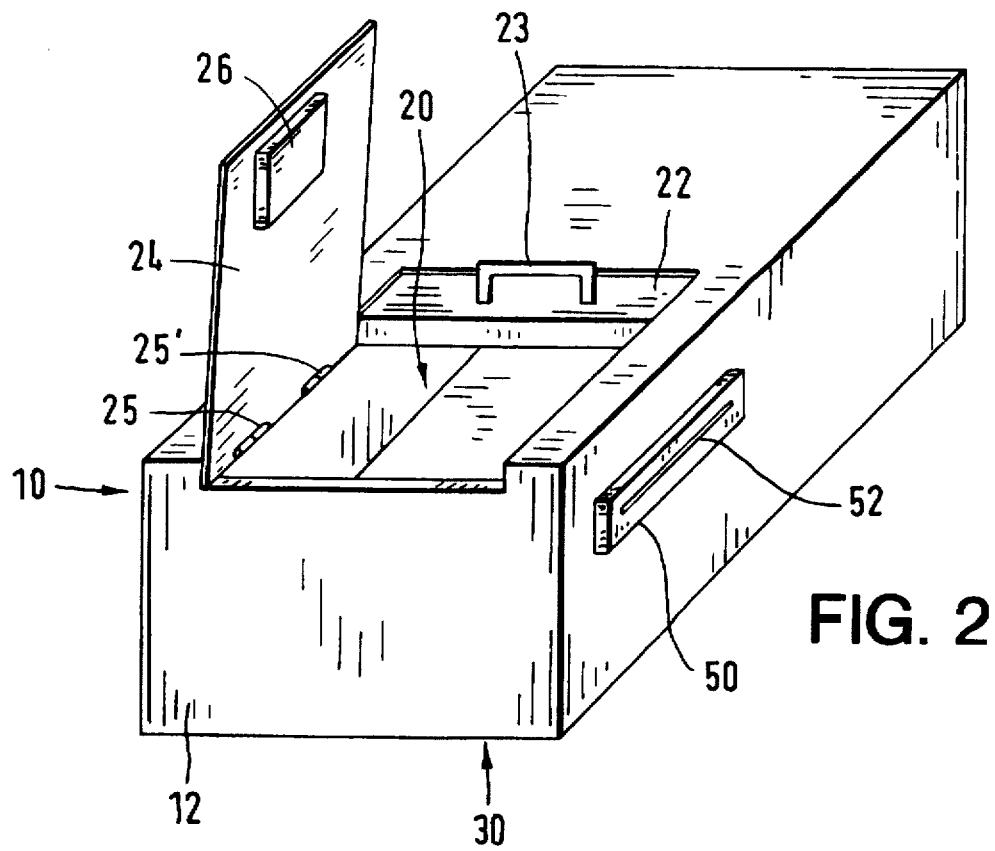
FIG. 2 is a view of a further embodiment of the refuse airlock according to the invention.

FIG. 2 illustrates a further embodiment of the refuse airlock 10 with a housing 12, according to the invention, in which an inlet 20 has a door or flap 24 in addition to the slide closure 22 with a handle 23. The inlet 20 is thus closable by means of the door 24 and the closure 22. In particular, the door 24 has two hinges 25, 25'.

A controllable interlock (not illustrated) comprises a lock 26 which is mounted or fixed on the door 24 and can prevent or lock or block the opening of the flap 26. In particular, the door 24 has a pin (not illustrated) on its side directed in the closed state toward the slide closure 22, which pin prevents the slide closure 22 being opened in the case of the door 24 not being completely closed.

In an embodiment which is not illustrated, the hinges 25, 25' are replaced by circular rigid hinges which engage in a side wall of the housing 12 of the refuse airlock 10. In particular, the interlock acts on these hinges and is arranged, in particular, behind a wall of the side wall of the housing. The interlock thus provides locking or blocking of the door 24 which is difficult to manipulate and thus increases the security against fraudulent use of the entire refuse airlock.

The refuse airlock 10 illustrated in FIG. 2 furthermore comprises a magnetic card recording device (not illustrated) with a scanning device 50 for scanning a magnetic card (not illustrated) introduced into a slot 52. The scanning device 50 is known per se and is not described in detail here. The magnetic card introduced is blocked in the scanning device 50, in particular during a discharge operation, and is only released again at the end of the discharge operation.

Data are stored on the magnetic card introduced, which data are compared by a comparison device (not illustrated) with data stored in a memory (not illustrated). In particular, these data contain characteristic data for identifying the card holder and possibly also security data which prevent forgery of the magnetic card.

The refuse airlock 10 comprises a chamber between the inlet 20 and the outlet 30. The shaping of the chamber is, in particular, cylindrical with a circular, oval or rectangular section, and the openings of the inlet 20 and the outlet 30 can, in particular, be adapted to the shaping of the chamber. In particular, the opening of the inlet 20 and/or of the outlet 30 can be circular or oval or rectangular.

In a further embodiment (not illustrated) of the refuse airlock according to the invention, a weighing device is provided for weighing the waste material introduced into a chamber of the refuse airlock.

In a further design of the refuse airlock according to the invention, a counting device is provided, which records or calculates the number of charging operations or the total quantity of waste material introduced, and which sets the interlock in a blocked or blocking state when a predetermined number or total quantity is reached.

The refuse airlock of the present invention is mounted, in particular, on a refuse skip, a refuse bin, a refuse container or a refuse hut or on a refuse chute. These are known per se and are therefore not described in detail. The dimensions of the refuse airlock according to the invention are adapted, in particular, to the internal and/or external dimensions of the refuse skip, the refuse bin, the refuse container or the refuse hut or the refuse chute.

A refuse discharge operation takes place, in particular, as follows:

a user introduces a magnetic card into a scanning device of a magnetic card device;

data from the magnetic card are recorded and compared by a comparison device with data stored in a memory;

in the event of the comparison being "successful", i.e. for example the user is authorized, a signal is transmitted for inhibiting or interrupting an interlock and a signal is transmitted to the charging device;

an inlet of the refuse airlock can thus be actuated or can thus be opened;

the user opens the inlet and thus simultaneously closes an outlet of the refuse airlock connected to the inlet;

the user introduces or inserts waste material into a chamber which connects the inlet and the outlet;

the user closes the inlet, as a result of which the outlet is opened and the waste material drops, for example, into a refuse bin arranged below the refuse airlock;

the inlet is again locked or blocked by the interlock;

if appropriate, a signal is transmitted to the scanning device in order to release the magnetic card again which is blocked therein.

The refuse airlock is ready for the next refuse-discharge operation.

Figure 3A:
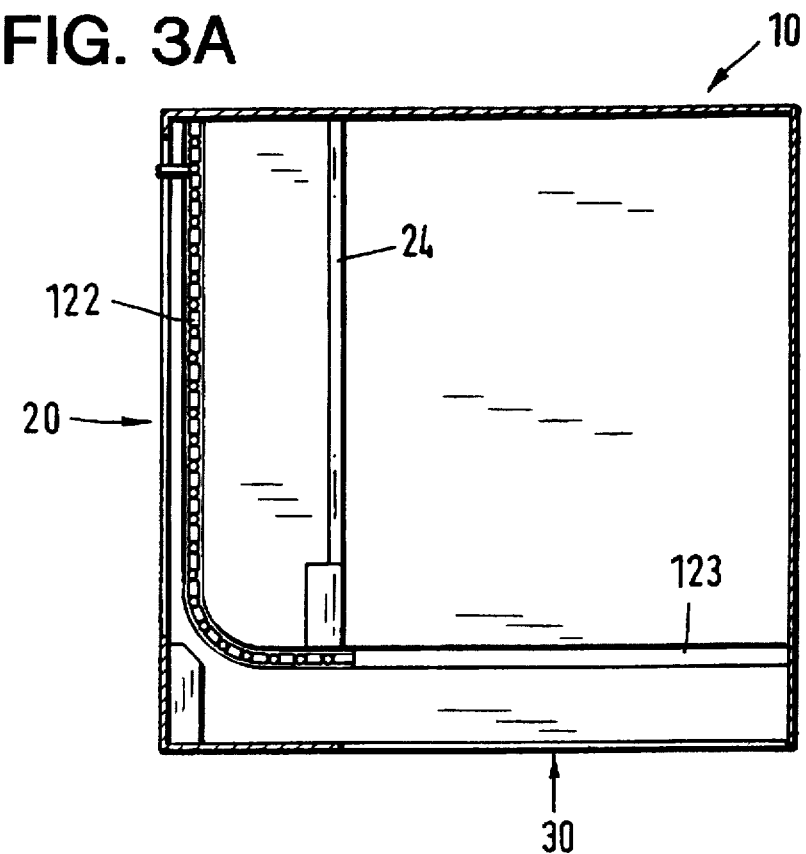
FIG. 3(A) is a sectional view of a further embodiment of the present invention with a closed inlet and an open outlet.
Figure 3B:
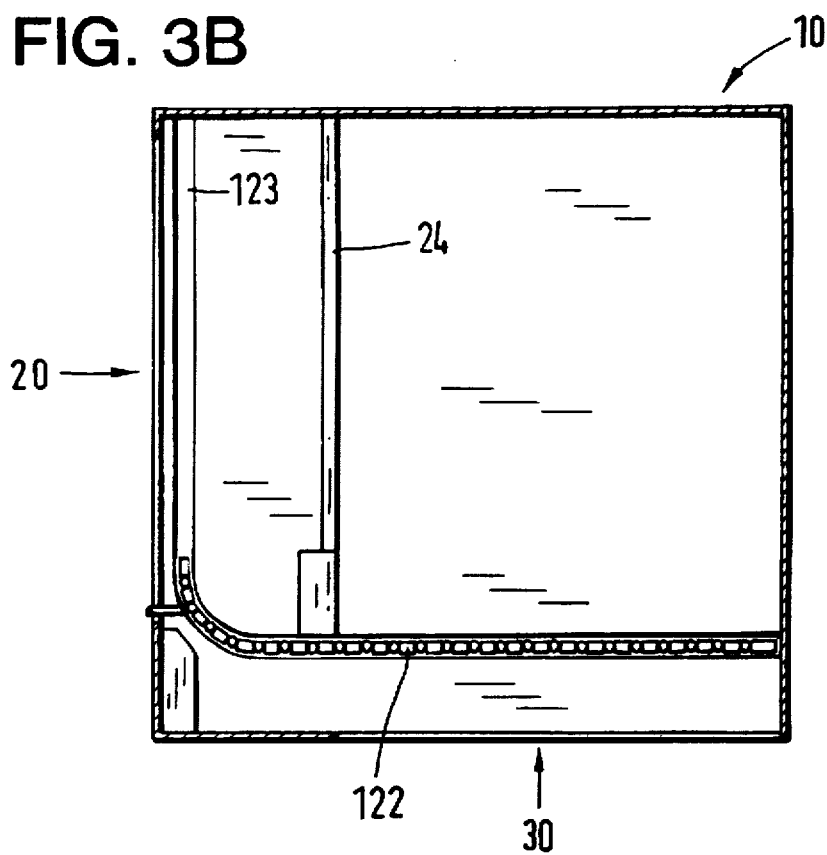
FIG. 3(B) is a sectional view of the embodiment shown in FIG. 3(a) with an open inlet and a closed outlet.

In the further embodiment shown in FIGS. 3(A) and 3(B), the inlet 20 and the outlet 30 comprise link closures 122, similar to a roller shutter comprising a plurality of links, which are, in particular, connected to one another. Furthermore, the link closures are designed, in particular, as a single, continuous link closure. The link closures or the link closure 122 slide or slides in grooves of rails 123 which are arranged, in particular, along the side walls of the refuse airlock. A Teflon film, graphite or the like is applied in the grooves and/or on the link closures in order to improve the sliding properties, i.e. the lubrication of the link closures or rails.

In the preferred embodiment illustrated in FIGS. 3(A) and (B), the inlet 20 comprising the link closure is arranged in a plane which is not parallel to the plane of the outlet 30, i.e. the inlet 20 is arranged at an angle relative to the outlet 30, the inlet 20 is preferably arranged in a substantially vertical part of the refuse airlock 10, whereas the outlet 30 is preferably arranged on a horizontal bottom of the refuse airlock 10, in particular near to the inlet.

In the embodiment shown in FIGS. 3(A) and (B), the first, in particular front, closure device 22 of the inlet 20 and the outlet 30 are designed as a link chain or roller shutter 122. The link chain 122 comprises closure elements which are connected to one another in an articulated or pivotable manner and are, in particular, of rod-like design and preferably form only very small gaps between adjacent closure elements. The closure elements are guided at their two end faces or ends in rails 123 running in parallel at the sides of the inlet 20 and the outlet 30. A second, in particular rear, closure device 24 is provided behind the first closure device 22. When the first closure device 22 is actuated by means of a handle (not shown), the closure elements slide along the rails 123, release the second closure device 24 and simultaneously close the outlet 30. When the inlet 20 is completely open and the outlet 30 is hence simultaneously fully closed, the second closure device 24 can be actuated or opened. Passing waste material through a simultaneously open first 22 and second 24 closure device and outlet 30 is thus impossible. In this embodiment, the opening of the inlet 20 and the outlet 30 have approximately the same areas.

Figure 4:
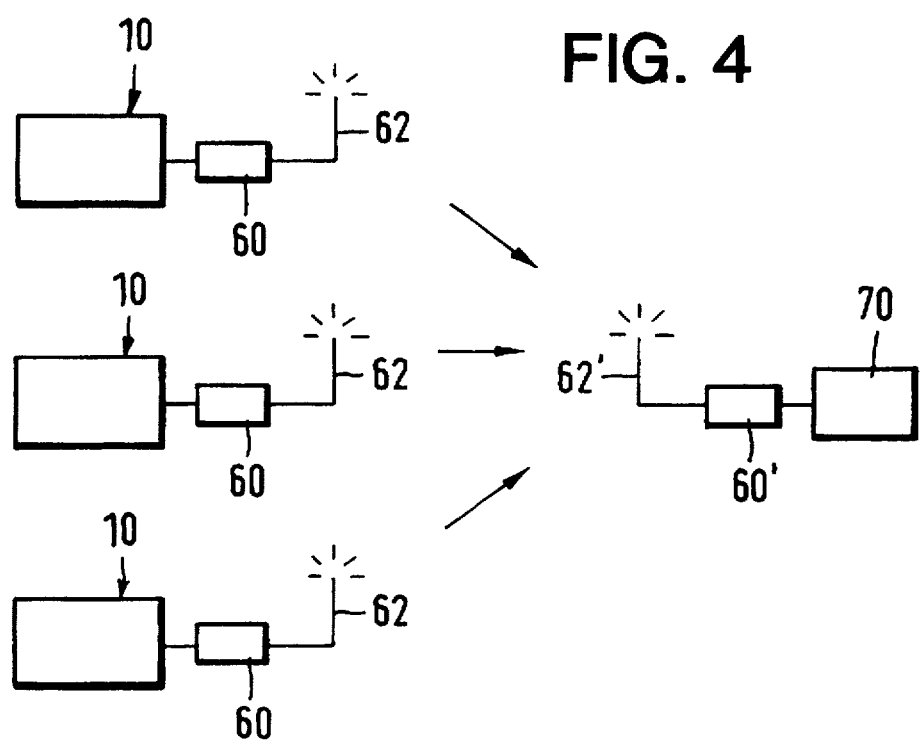
FIG. 4 is a diagrammatic view of a further embodiment of the present invention.

In the embodiment shown in FIG. 4, the refuse airlock 10 comprises a data transmission device. The data transmission device comprises radio devices 60, 60', aerials, 62, 62' and an evaluation device 70. The data recorded by the payment device can thus be transmitted via radio to an evaluation device located, for example, at a central evaluation point. It is thus advantageously possible to combine information or data from one or more refuse airlocks centrally in one place without having to read off the data on site. The radio devices 60, 60' can, in particular, comprise radio telephones or the like which are known per se.

The data or information transmitted can comprise, in particular:

the number of charging operations for one particular refuse airlock;

an ID code for the airlock or refuse bin which designates, for example, the location of the airlock, relates to the type of bin, etc.;

a filling level of the bin which can be determined, for example, by the number of filling or refuse-discharge operations, by the predetermined volume of the chamber of the airlock and by the size of the refuse bin;

a signal which indicates that the refuse bin or the refuse container is full, with the result that the refuse collection, for example, only has to empty the refuse bins when this signal is transmitted;

a date and/or a time;

a total number of charges carried out;

an ID code for individual users and/or a number of charges per individual user;

a total weight of refuse inserted in the refuse bin, etc.

In the embodiments which are not shown, the data transmission can also take place via a data network (e.g. the internet), via the telephone network, on site via a data carrier (e.g. a diskette or a magnetic tape) and/or by means of an interface via a (in particular portable) computer.

In a further embodiment (not shown), one data transmission device is common to a plurality of adjacently arranged refuse airlocks.

We claim:

1. A refuse airlock (10) for use with refuse containers comprising:

a refuse chamber of a predetermined volume;

an inlet (20) communicating with said refuse chamber;

a first inlet closure device (22) movably mounted in proximity to said inlet (20) for selectively opening and closing said inlet;

a second inlet closure device (24) movably mounted in proximity to said inlet (20) for selectively opening and closing said inlet (20) after an initial opening of said first inlet closure device (22);

an outlet (30) spaced from said inlet (20) and communicating with said chamber;

an outlet closure (32) movably mounted in proximity to said outlet (30) for selectively opening and closing said outlet (30);

means for preventing simultaneous opening of the inlet (20) and the outlet (30); and at least one controllable interlock for selectively locking at least said second inlet closure device (24) in dependence on a payment calculation operation.

2. The refuse airlock as claimed in claim 1, wherein the second inlet closure device (24) is only accessible when the first inlet closure device (22) is open.

3. The refuse airlock as claimed in claim 2, wherein the first inlet closure device (22) is not closable when the second inlet closure device (24) is open.

4. The refuse airlock as claimed in claim 3, wherein the first inlet closure device (22) is connected to the outlet closure device (32) via at least one wire cable (42) guided around deflection rollers (40).

5. The refuse airlock as claimed in claim 3, wherein the first inlet closure device (22) and the outlet closure device (32) comprise closure elements (122) connected to one another in an articulated manner.

6. The refuse airlock as claimed in claim 5, wherein the closure elements (122) are of elongate design and are guided in rails (123) at their end faces.

7. The refuse airlock as claimed in claim 1, wherein a restoring mechanism is provided, which prestresses at least one of the inlet and the outlet into an original position.

8. The refuse airlock as claimed in claim 1, further comprising a payment device connected to the controllable interlock for carrying out the payment calculation operation and wherein the payment device has a charging memory for storing cost calculation operations.

9. The refuse airlock as claimed in claim 1, further comprising a payment device connected to the controllable interlock for carrying out the payment calculation operation and wherein the payment device has a magnetic card recording device.

10. The refuse airlock as claimed in claim 9, wherein the magnetic card recording device comprises a scanning device (50) for scanning data of a magnetic card, a memory and a comparison device, said comparison device comparing the scanning data from the scanning device (50) with that from the memory.

11. The refuse airlock as claimed in claim 10, wherein the magnetic card recording device comprises an input unit for the input of a code, a memory and a comparison device, the comparison device comparing the code of the input unit with data stored in the memory.

12. The refuse airlock as claimed in claim 1, further comprising a payment device connected to the controllable interlock for carrying out the payment calculation operation and wherein the payment device has a code recording device for recording a code.

13. The refuse airlock as claimed in claim 1, further comprising a payment device connected to the controllable interlock for carrying out the payment calculation operation and wherein the payment device comprises a coin insertion device.

14. The refuse airlock as claimed in claim 1, further comprising a payment device connected to the controllable interlock for carrying out the payment calculation operation and wherein the payment device comprises a substraction device and a reading/writing device for reading in a credit, a subtraction device subtracting a unit from the credit and entering the new amount.

15. The refuse airlock as claimed in claim 1, wherein the refuse airlock is used with a refuse container disposed in proximity to the outlet (30) and wherein the data transmitted comprise a date, a time, a code identifying an individual payment device, a code identifying an individual refuse airlock, a filling level of the refuse container, a user code, a cost calculation operation for a predetermined user code and a weight of waste material inserted.

16. A refuse airlock (10) for refuse containers, comprising:

an inlet (20) for introducing waste material;

an outlet (30) for discharging the waste material;

an inlet closure device (22) movably mounted in proximity to said inlet (20) for selectively opening and closing said inlet (20);

an outlet closure device (32) movably mounted in proximity to said outlet (30) for selectively opening and closing said outlet (30);

means for preventing simultaneous opening of the inlet closure device (22) and the outlet closure device (32);

at least one controllable interlock for selectively locking at least one of the inlet closure device (22) and the outlet closure device (32);

a weighing device for weighing the waste material introduced into the refuse airlock (10); and a payment device communicating with said interlock and said weighing device for controlling the interlock in dependence on a payment calculation operation based on the weight of the waste material introduced into the refuse airlock (10).

17. A refuse airlock (10) for refuse containers, comprising:

an inlet (20) for introducing waste material;

an outlet (30) for discharging the waste material;

an inlet closure device (22) movably mounted in proximity to said inlet (20) for selectively opening and closing said inlet (20);

an outlet closure device (32) movably mounted in proximity to said outlet (30) for selectively opening and closing said outlet (30);

means for preventing simultaneous opening of the inlet closure device (22) and the outlet closure device (32);

at least one controllable interlock for selectively locking at least one of the inlet closure device (22) and the outlet closure device (32);

an identification device which provides the waste material introduced into the refuse airlock (10) with an identification; and a payment device for controlling the selective locking of the interlock in dependence on a payment calculation operation.

18. A refuse airlock comprising:

an inlet (20) for introducing waste material;

an outlet (30) for discharging the waste material;

an inlet closure device (22) movably mounted in proximity to said inlet (20) for selectively opening and closing said inlet (20);

an outlet closure device (32) movably mounted in proximity to said outlet (30) for selectively opening and closing said outlet (30);

means for preventing simultaneous opening of the inlet closure device (22) and the outlet closure device (32);

at least one controllable interlock for selectively locking at least one of the inlet closure device (22) and the outlet closure device (32);

a payment device for controlling the selective locking of the interlock in dependence on a payment calculation operation, the payment device comprising a substraction device and a reading/writing device for reading in a credit, the subtraction device subtracting a unit from the credit and entering a new amount, the payment device further comprises a data transmission device (60, 60', 62, 62') for transmitting data to a data recording device (70), the data transmission device (60, 60', 62, 62') transmitting the data by a data transmission network.

* * * * *